United States Patent
Cao et al.

(10) Patent No.: US 7,496,403 B2
(45) Date of Patent: Feb. 24, 2009

(54) APPARATUS AND METHOD FOR TESTING AN IMPLANTABLE MEDICAL DEVICE AND SENSING PARAMETER SETTINGS

(75) Inventors: Jian Cao, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 244 days.

(21) Appl. No.: 11/217,050

(22) Filed: Aug. 31, 2005

(65) Prior Publication Data

US 2007/0049982 A1   Mar. 1, 2007

(51) Int. Cl.
*A61N 1/00* (2006.01)
(52) U.S. Cl. .................... 607/27; 600/510; 607/28
(58) Field of Classification Search ............... 607/27, 607/28, 30; 600/510
See application file for complete search history.

(56) References Cited

U.S. PATENT DOCUMENTS

| | | | |
|---|---|---|---|
| 6,311,089 B1 | 10/2001 | Mann et al. | |
| 6,366,812 B1 | 4/2002 | Levine et al. | |
| 2004/0015197 A1* | 1/2004 | Gunderson | 607/27 |
| 2004/0260348 A1* | 12/2004 | Bakken et al. | 607/9 |

* cited by examiner

*Primary Examiner*—Carl H Layno
*Assistant Examiner*—Brian T Gedeon
(74) *Attorney, Agent, or Firm*—Michael C. Soldner

(57) ABSTRACT

In an apparatus and a method for use in setting a sensing parameter of an implantable medical device (IMD) of a patient, cardiac data corresponding to a cardiac episode experienced by the patient is obtained from a sensing electrode associated with the IMD. At the time the cardiac data is obtained, the IMD is operated at a first setting of the sensing parameter. Based upon this cardiac data, a simulation is performed of cardiac event identification if the IMD were operated at a different setting of the sensing parameter. The simulated cardiac event identification performance of the IMD is then reported.

24 Claims, 7 Drawing Sheets

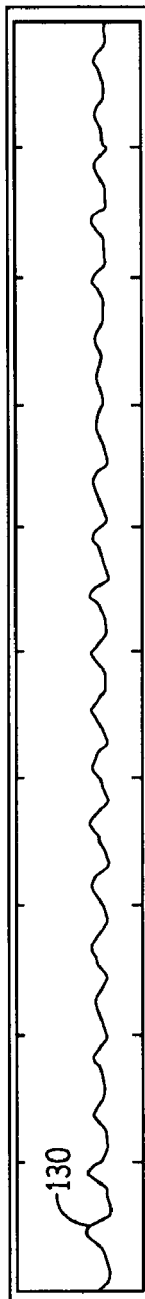
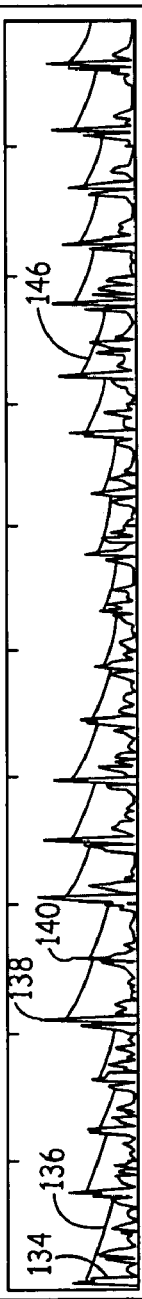
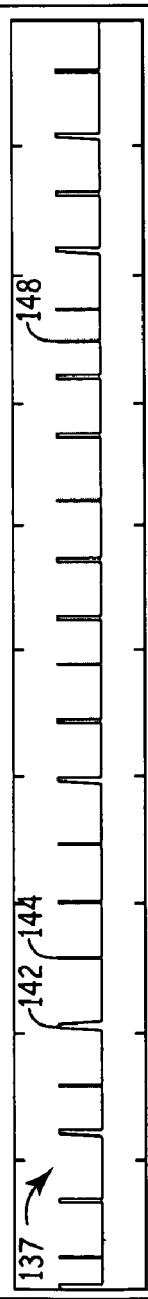
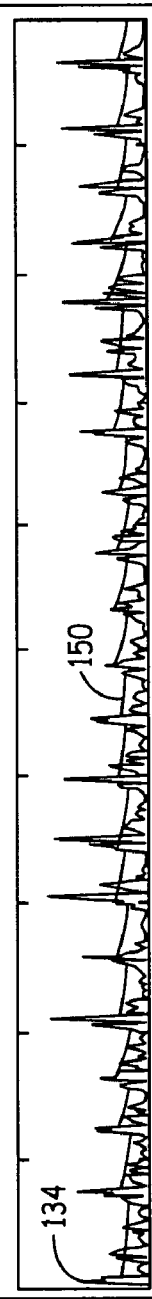
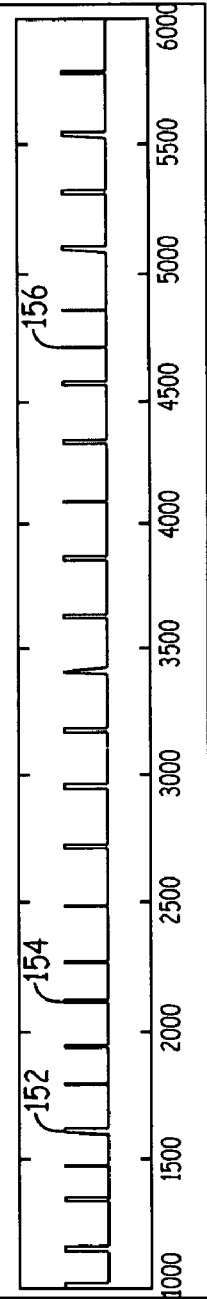

0.3 mV 0.45 mV 0.6 mV 1.2 mV

Sense Markers

APPARATUS AND METHOD FOR TESTING AN IMPLANTABLE MEDICAL DEVICE AND SENSING PARAMETER SETTINGS

BACKGROUND OF THE INVENTION

The present invention relates generally to the field of implantable medical devices, and more particularly to an apparatus and method for testing an implantable medical device, such as an implantable cardioverter defibrillator (ICD), following its implant into a patient and guiding the setting of its sensing parameters.

An implantable cardioverter defibrillator (ICD) provides therapies for maintaining and restoring normal cardiac rhythms by cardiac pacing or by delivering electrical shock therapy for cardioverting or defibrillating the heart. The ICD is implanted under the skin of the user, and one or more electrical leads connected to the ICD are inserted into or in proximity to the heart of the patient. The leads carry current from the ICD to the heart tissue to stimulate the heart using either low energy pacing pulses or high-energy cardioversion/defibrillation shocks. The leads are also used for sensing electrogram (EGM) signals from the heart that are used by the ICD to determine a therapy to be delivered.

Within the ICD, sense amplifiers coupled to the leads amplify the EGM signals from the electrodes. The amplified EGM signal is then filtered, rectified, and level-detected to sense intrinsic depolarizations of the atria (referred to as P-waves) and the ventricles (referred to as R-waves).

Single chamber ICDs use a single lead placed in the right ventricle to treat ventricular arrhythmia. Dual chamber ICDs treat ventricular arrhythmia (and in some cases atrial arrhythmia as well), and have one lead placed in the right ventricle and a second lead placed in the right atrium. In some cases, a third lead may be placed to stimulate the left ventricle (e.g., in the coronary sinus).

For dual chamber detection algorithms in ICDs, the ICD delivers a therapy based upon the sensed P-waves from the atrial lead and the R-waves from the ventricular lead, which can include antitachycardia pacing (ATP), cardioversion or defibrillation. The effectiveness of the ICD in treating tachyarrhythmia depends upon the ability to accurately sense P-waves and R-waves with the atrial and ventricular leads, respectively.

During the implant of an ICD into a patient, it is common to test the ICD and its respective sensor leads and electrodes. This is generally accomplished by inducing a cardiac episode, such as ventricular fibrillation (VF), in the patient and monitoring the patient and the ICD to determine if the ICD properly detects the cardiac episode. In some patients, however, spontaneous cardiac episodes are characterized by very small amplitudes, unlike those of induced cardiac episodes. Thus, it is helpful to confirm operability at a lower sensitivity setting than the ICD's default setting.

Additionally, the implanted electrodes are at their most sensitive immediately following their initial implant. This results because tissue grows over the implanted electrodes soon after their implant, which changes the frequency content and/or amplitude of the sensed EGM signal.

Thus, during the initial testing of the ICD, it is common to reprogram the ICD to have a lower sensitivity setting than its default sensitivity setting to better ensure operability in the weeks and years following implant. Unfortunately, a common user error associated with this procedure is the failure to return the sensitivity setting back to its default value. This error may result in significant undersensing of R-waves during a cardiac episode, which may in turn result in the failure or delay in detecting the episode.

Most conventional ICDs do not provide the physician with information about a safety margin for a particular sensitivity setting. Rather, the physician is left to review the large quantity of recorded EGM data when trying to select a sensitivity setting that best prevents both undersensing and oversensing.

Accordingly, a need exists for an improved apparatus and method for testing the operability and sensitivity settings of an ICD.

BRIEF SUMMARY OF THE INVENTION

In setting a sensing parameter of an implantable medical device (IMD) of a patient, cardiac data corresponding to a cardiac episode experienced by the patient is obtained from a sensing electrode associated with the IMD. At the time the cardiac data is obtained, the IMD is operated at a first setting of the sensing parameter. Based upon this cardiac data, a simulation is performed of cardiac event identification if the IMD were operated at a different setting of the sensing parameter. The simulated cardiac event identification performance of the IMD is then reported.

BRIEF DESCRIPTION OF THE DRAWINGS

FIGS. 5A-F and 6A-6F are graphs of various cardiac parameters as a function of time for illustrating the how a sensitivity setting of an ICD may affect its ability to detect a cardiac episode.

DETAILED DESCRIPTION

Figure 1:
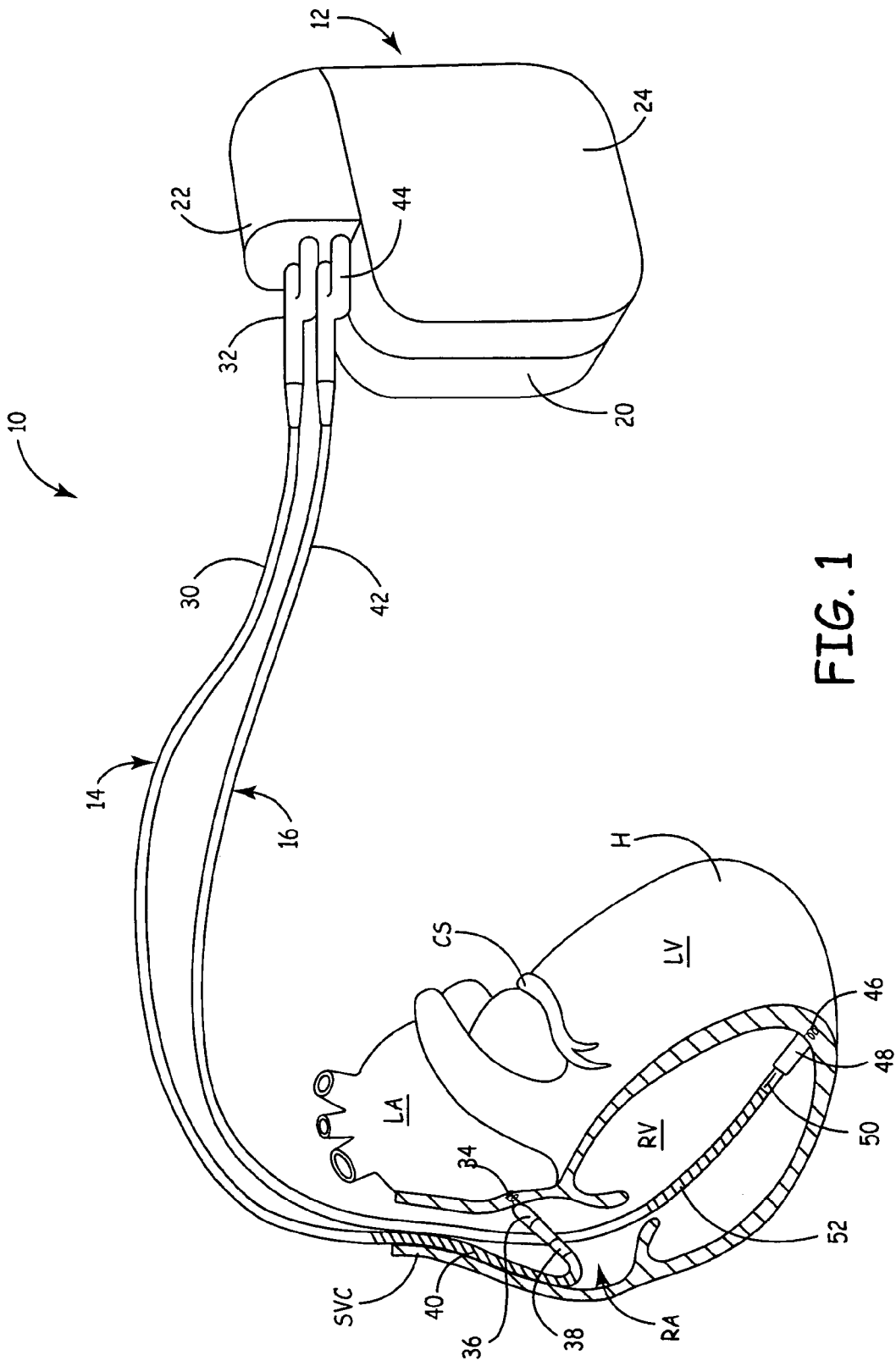
FIG. 1 is a diagram of an ICD and lead set of a type in which the present invention may be practiced.

FIG. 1 illustrates an implantable medical device 10, which provides dual chamber pacing and cardioversion/defibrillation therapy to heart H. In FIG. 1, heart H is shown in a partially cutaway view illustrating right atrium RA, left atrium LA, right ventricle RV, left ventricle LV, coronary sinus CS, and superior vena cava SVC.

Implantable medical device (IMD) 10 includes implantable cardioverter defibrillator (ICD) 12, right atrial (RA) lead 14, and right ventricular (RV) lead 16. As shown in FIG. 1, ICD 12 includes housing or canister 20, header 22, and can electrode 24. The circuitry and power source of ICD 12 are located within housing 20. The circuitry communicates with leads 14 and 16 through electrical connectors within header 22. Can electrode 24 is formed on or is a part of the outer surface of housing 20, and acts as an electrode with respect to one or more of the electrodes carried by leads 14 and 16.

RA lead 14 is passed through superior vena cava SVC into right atrium RA of heart H. RA lead 14 includes lead body 30, connector 32, distal tip attachment mechanism 34, tip electrode 36, ring electrode 38, and SVC coil electrode 40. Lead body 30 contains insulated conductors that extend from connector 32 to electrodes 36, 38, and 40. Connector 32 is a bifurcated connector that is inserted into connection bores within header 22 to provide electrical connection between electrodes 36, 38, and 40 and circuitry within ICD 12. Tip electrode 36 and ring electrode 38 are used to deliver pacing pulses to right atrium RA as well as to sense EGM signals within right atrium RA. Coil electrode 40 may be used to deliver a high voltage cardioversion or defibrillation pulse to superior vena cava SVC and right atrium RA. Can electrode 24 is used as the other electrode when a cardioversion/defibrillation pulse is delivered.

RV lead 16 is passed into right atrium RA, and then through the tricuspid valve into right ventricle RV. RV lead 16 includes lead body 42, connector 44, distal tip attachment mechanism 46, tip electrode 48, ring electrode 50, and coil electrode 52. In some embodiments, a SVC coil can be located on RV lead 16 rather than RA lead 14. Lead body 42 of RV lead 16 contains electrically insulated conductors that extend from connector 44 to tip electrode 48, ring electrode 50 and coil electrode 52. At the proximal end of RV lead 16, bifurcated connector 44 is inserted into a pair of connection bores of header 22 to provide electrical connection between the circuitry within housing 20 and electrodes 48, 50, and 52. Tip electrode is placed in contact with the apex of right ventricle RV, and is fixed in placed by attachment mechanism 46, which may be, for example, a screw or tined fastener.

Tip electrode 48 and ring electrode 50 form a true bipolar electrode pair which can be used for applying pacing pulses to right ventricle RV and sensing EGM signals representative of electrical activity in right ventricle RV. Coil electrode 52 is used, in conjunction with can electrode 24, to apply high voltage cardioversion or defibrillation shock in order to halt ventricular arrhythmia. Together with tip electrode 48, coil electrode 52 also forms an integrated bipolar sensing electrode pair, which can be used to sense EGM signals.

While a particular ICD and lead system is illustrated in FIG. 1, methodologies included in the present invention may be adapted for use with any single chamber, dual chamber, or multi-chamber ICD or pacemaker system or other cardiac monitoring device.

Figure 2:
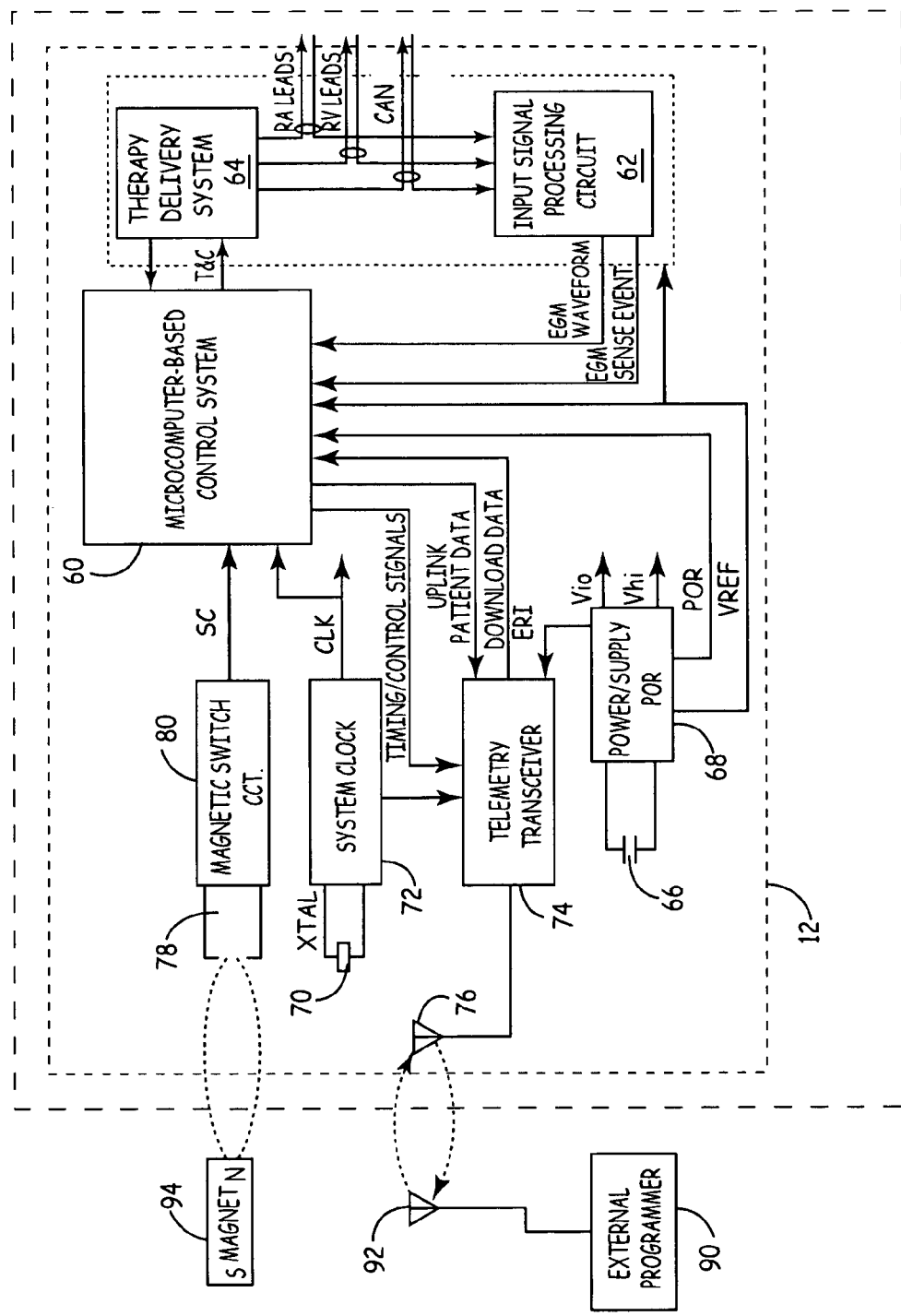
FIG. 2 is a block diagram of the ICD illustrated in FIG. 1.

FIG. 2 is an electrical block diagram of ICD 12 that provides delivery of therapy through leads 14 and 16 shown in FIG. 1. As shown in FIG. 2, ICD 12 includes microcomputer-based control system 60, input signal processing circuit 62, therapy delivery system 64, battery 66, power supply/power on reset (POR) 68, crystal oscillator 70, system clock 72, telemetry transceiver 74, antenna 76, switch 78, and magnetic switch circuit 80. Also shown in FIG. 2 are external programmer 90 and antenna 92 (which communicate with ICD 12 through antenna 76 and transceiver 74), and magnet 94 (which interacts with ICD 12 through switch 78 and magnetic switch circuit 80).

Control system 60 controls the functions of ICD 12 by executing firmware and program software algorithms stored in associated RAM and ROM. Control system 60 may also include additional circuitry including a watchdog circuit, a DMA controller, a block mover/reader, a CRC calculator, and other specific logic circuitry coupled together by an on-chip data bus, address bus, power, clock, and control signal lines. Control and timing functions can also be accomplished in whole or in part with dedicated circuit hardware or state machine logic rather than a programmed microcomputer.

Input signal processing circuit 62 receives signals from RA lead 14 and RV lead 16. The outputs of input signal processing circuit 62 include digitized EGM waveforms and sense event signals derived from EGM signals sensed by leads 14 and 16.

Input signal processing circuit 62 includes at least one channel for sensing and processing cardiac signals from electrodes carried by leads 14 and 16. Each channel typically includes a sense amplifier for sensing specific cardiac events and an EGM amplifier for providing the EGM waveform signal to control system 60, where the EGM waveform is stored. Input signal processing circuit 62 can be implemented with analog circuitry or with a digital signal processor.

Therapy delivery system 64 delivers cardiac pacing pulses to leads 14 and 16 as directed by control of control system 60. Delivery of pacing pulses is controlled in part by the selection of programmable pacing intervals, which can include atrial-atrial (A-A), atrial-ventricular (A-V), and ventricular-ventricular (VV) intervals. Therapy delivery system 64 also includes circuitry for delivering cardioversion/defibrillation therapy using SVC coil electrode 40, RV coil electrode 52, and can electrode 24.

Electrical energy for ICD 12 is supplied from battery 66 through power supply/POR circuit 68. This includes power to operate the circuitry controlling operation of ICD 12, as well as electrical stimulation energy for delivery to heart H, and power for telemetry signal transmissions. Power supply/POR circuit 68 provides low voltage power Vlo, POR signal, reference voltage VREF, elective replacement indicator signal ERI, and high voltage power Vhi (for cardioversion/defibrillator capabilities).

Crystal oscillator 70 and system clock 72 provide clock signals for operation of the digital logic within ICD 12. Control system 60 uses the clock signals for various time measurements, and produces timing and control signals based on the clock signals.

Uplink and downlink telemetry capabilities are provided through transceiver 74 and antenna 76. External programmer 90 can receive stored EGM data, as well as real-time generated physiologic data and non-physiologic data from control system 60. In addition, programming data can be supplied from external programmer 90 to control system 60.

Magnetic field sensitive switch 78 and magnetic switch circuit 80 issue a switch closed (SC) signal to control system 60 when magnet 94 is positioned over the subcutaneous implanted ICD 12. This indicates to ICD 12 that a communication device is present.

Figure 3:
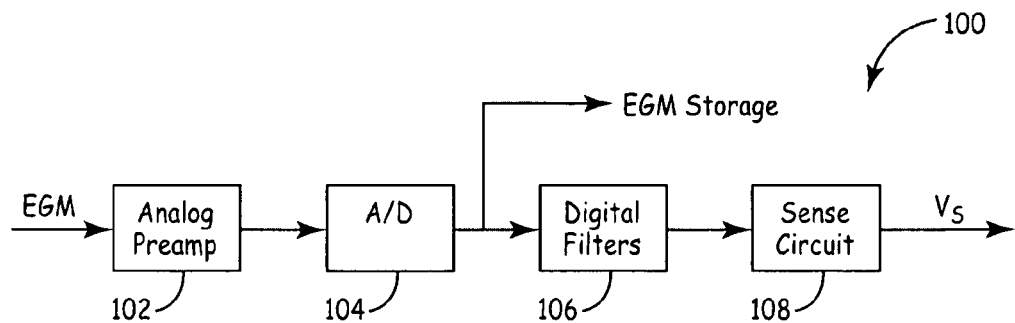
FIG. 3 is a block diagram illustrating EGM signal processing in the ICD illustrated in FIG. 1.

FIG. 3 is a block diagram of signal processing channel 100, which forms a part of input signal processing circuit 62. Channel 100 includes EGM amplifier 102, analog-to-digital converter 104, digital filter 106, and sense circuit 110. In monitoring ventricular activity, channel 100 produces a ventricular sense signal VS in response to a detected R-wave in an analog ventricular electrogram (EGM) signal.

The EGM signal is received from one or more of the electrodes associated with ICD 12. For example, EGM signal may be received from right ventricle tip electrode 48 and right ventricle ring electrode 50 or from right ventricle tip electrode 48 and right ventricle coil electrode 52. Electrodes 48 and 50 are closely spaced, similarly sized electrodes. Preamplifier 102 amplifies the analog EGM signal, and further filters the EGM signal using a wide band-pass filter. Preferably, preamplifier 102 is a differential amplifier that produces as an output the difference in potential between electrodes 48 and 50 or electrodes 48 and 52. This provides common mode rejection for potentials present simultaneously at both electrodes. The signal is then sampled and converted by analog-to-digital converter 104 for storage by control system 60 in memory and/or for subsequent signal processing. Although the EGM signal is shown in FIG. 3 as being from the output of analog-to-digital converter 104 (and analog preamplifier 102), the stored data may be obtained from other amplifiers, either analog or digital, of ICD 12. Because ICD 12 is limited in storage space, ICD 12 may preserve space by saving only those EGM signals that correspond to a period about a significant cardiac episode. Another alternative is to just save sense markers (indicators that a cardiac event was detected) at different sensitivity settings.

Digital filter 106 further filters the signal using a narrow band-pass filter and rectifies the signal. The signal is then compared to a sensing level by sense circuit 108, and a V-sense pulse is produced when the signal exceeds a sensitivity setting of sense circuit 108. The sensitivity setting should be set at a level so that every R-wave is detected, while P-waves (representing atrial depolarization), T-waves, and other sources of electrical noise do not cause a V-sense pulse to be produced.

FIG. 3 illustrates signal processing channel 100 as a digital implementation of a sense amplifier. However, the present invention contemplates the use of analog circuitry as well. Additionally, while a single channel 100 is illustrated in FIG. 3, input processing circuit 62 may include multiple channels operating at the same or different sensing parameters.

It is common practice to confirm the operability of a newly implanted ICD prior to release of the patient so that any necessary corrective actions can be performed at that time. In testing the ICD, a cardiac event is induced in the patient to determine whether the ICD properly detects and treats the event. However, because induced cardiac events may have a greater amplitude than spontaneous cardiac events, it is helpful to test the ICD at a lower sensitivity than its default sensitivity setting. Additionally, the implanted electrodes are at their greatest sensitivity immediately following their initial implant. Tissue begins growing over the electrodes shortly after their implant and changes the frequency content and/or amplitude of any sensed EGM signal. Thus, during the initial testing of the ICD, it is common to reprogram the ICD to have a lower sensitivity setting (e.g., 1.2 millivolts) than its default sensitivity setting (e.g., 0.3 millivolts) to better ensure operability in the weeks and years following implant. Unfortunately, a common user error associated with this procedure is the failure to return the sensitivity setting back to its default value. This error may result in significant undersensing of R-waves during a cardiac episode, which may in turn result in the failure or delay in detecting the episode.

Figure 4:
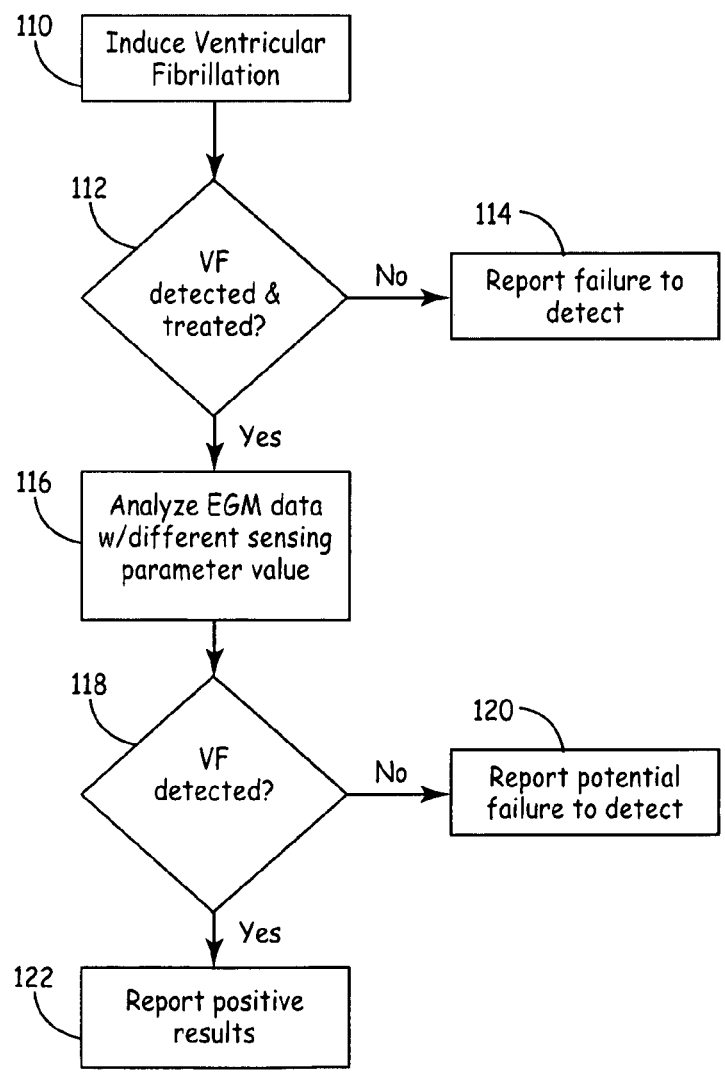
FIG. 4 is a flow chart illustrating a method in accord with the present invention for testing the operability of an ICD and respective leads and sensor electrodes following implant into a patient.

FIG. 4 is a flow chart illustrating a method in accord with the present invention for testing ICD 12 and its respective leads and sensor electrodes following implant into a patient. The method of FIG. 4 may be implemented in firmware and/or hardware in ICD 12 itself, external programmer 90 or similar device, a remote computer connected to external programmer 90 by a communication protocol, or a combination thereof.

In accord with the present invention, and unlike with the conventional test procedure, ICD 12 need not be reprogrammed to have a lower sensitivity setting for this test procedure. Rather, ICD 12 is operated at its default sensitivity setting. At step 110, a cardiac episode, such as ventricular fibrillation, is induced in the patient.

With ICD 12 operating at its default sensitivity setting, the patient and ICD 12 are both monitored at step 112, either by a physician or automatically (e.g., by ICD 12, external programmer 90 or similar device, remote computer connected to external program 90 by a communication protocol, or a combination thereof), to determine if ICD 12 detects the ventricular fibrillation.

If the VF is not properly detected, NO in step 112, the failure of ICD 12 to detect the ventricular fibrillation is automatically reported (e.g., by ICD 12, external programmer 90 or similar device, remote computer connected to external program 90 by a communication protocol, or a combination thereof) to the physician at step 114. The cause of a misdetection may include any of a number of electrical or mechanical problems, including a poorly positioned lead and/or electrode, a broken lead and/or electrode, or even possibly a faulty ICD 12.

If, on the other hand, the ventricular fibrillation is properly detected and treated, then at steps 116 and 118, the EGM data used to detect the failure is analyzed to simulate, or predict, how ICD 12 would have reacted had it been programmed with a lower sensitivity. The simulation is performed by varying parameters associated with digital filters 106 (FIG. 3) and determining whether a V-sense pulse would be produced by the EGM data if a lower sensitivity were used. In this way, by varying the parameters associated with filters 106 to simulate how the data would be detected using another sensitivity level or levels, ICD 12 need not be reprogrammed at all, and no risk exists that the physician will fail to reprogram ICD back to its default settings. If it is determined that ICD 12 would not have detected the ventricular fibrillation had it been programmed with a different sensitivity, at step 120 this potential underdetection is reported to the physician. If, however, it is determined that the ventricular fibrillation would have been detected, that positive operability result is reported to the physician at step 122. In some embodiments, steps 116, 118, and 120 may be performed regardless of whether ventricular fibrillation was properly detected and treated at step 112. Each of steps 116, 118, and 120 may be implemented in firmware and/or hardware in ICD 12 itself, external programmer 90 or similar device, a remote computer connected to external programmer 90 by a communication protocol, or a combination thereof.

Typically, the default sensitivity setting for the ventricular EGM signal is 0.3 millivolts. But, for purposes of testing ICD 12 at implant, the sensitivity setting of ICD 12 is commonly set to 1.2 millivolts. FIGS. 5A-5F (collectively FIG. 5) and 6A-6F (collectively FIG. 6) are graphs of various cardiac parameters as a function of time for illustrating the effects that these two sensitivity settings have on the ability of ICD 12 to detect a cardiac episode. FIG. 5 corresponds to a first example, while FIG. 6 corresponds to a second example.

Shown in FIGS. 5A and 5B are simulated ECG signal 130 and simulated ventricular EGM signal 132, respectively. In FIG. 5C, filtered signal 134 represents digitally band-pass filtered and rectified ventricular EGM signal 132, or the signal at the output of digital filters 106 of FIG. 3. Also shown in FIG. 5C is threshold signal 136 determined as a function of a 1.2 millivolts sensitivity setting for ICD 12. Threshold signal 136 is a variable value signal having peak values determined as a percentage of the amplitudes of sensed R-waves. Following each of these peak values, the amplitude of threshold signal 136 decays toward the sensitivity setting, which is 1.2 millivolts in this example. Shown in FIG. 5D is ventricular sense signal 137 corresponding to signals 134 and 136. In particular, a pulse or sense marker is registered in ventricular sense signal 137 each time a R-wave is detected in filtered EGM signal 134. Essentially, the occurrence of an R-wave is indicated at times when filtered EGM signal 134 exceeds 1.2 millivolts threshold signal 136. For example, peaks 138 and 140 of filtered EGM signal 134 correspond to times where filtered EGM signal 134 exceeds 1.2 millivolts threshold signal 136, and thus also correspond with sense markers 142 and 144 of ventricular sense signal 137.

Several circumstances exist, however, where the ventricular EGM sense electrodes oversense R-waves (i.e., detect false R-waves). These circumstances include the sensing of T-waves or P-waves as R-waves, and other sources of electrical noise. For example, in FIG. 5C, peak 146 corresponds to a time when filtered EGM signal 134 exceeds 1.2 millivolts threshold signal 136 but not to an R-wave. Nonetheless, sense marker 148 is recorded in ventricular sense signal 137. Oversensing of a single R-wave as shown in FIGS. 5C and 5D should not be troublesome. As this number increases, however, ICD 12 may begin improperly diagnosing cardiac arrhythmias. The derivation of ventricular sense signal 137 occurs in sense circuit 108 of FIG. 3. FIG. 5E re-plots filtered EGM signal 134 of FIG. 5C along with threshold signal 150 determined as a function of a 0.3 millivolts sensitivity setting for ICD 12. Shown in FIG. 5F is a ventricular sense function 152 corresponding to the to the signals 134 and 150. As expected, more oversensing occurs with the greater sensitivity setting, i.e., at 0.3 millivolts. In particular, sense markers 152, 154, and 156 indicate the occurrence of R-waves where they should not. In the example of FIG. 5, acceptable sensing (that is, sensing that will result in acceptable detection of cardiac episodes) occurs at both the 0.3 millivolts sensitivity setting and 1.2 millivolts sensitivity setting.

Figure 6A:
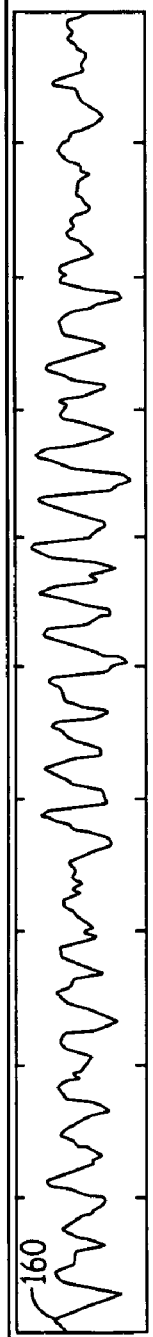
Figure 6B:
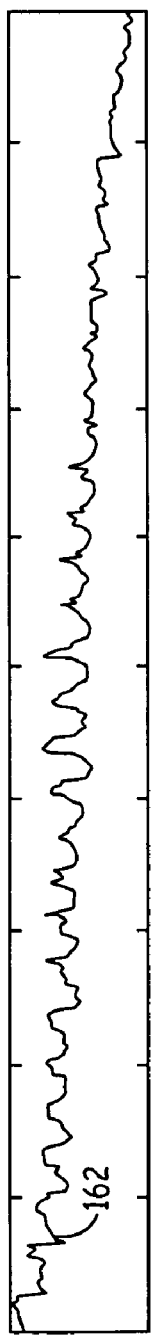
Figure 6C:
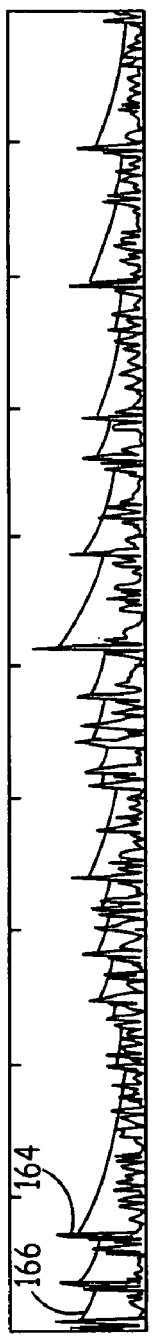
Figure 6D:
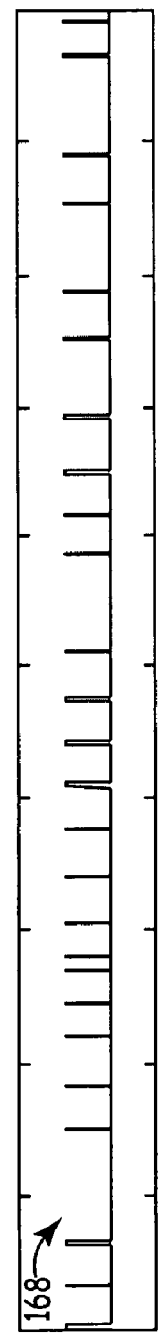
Figure 6E:
Figure 6F:
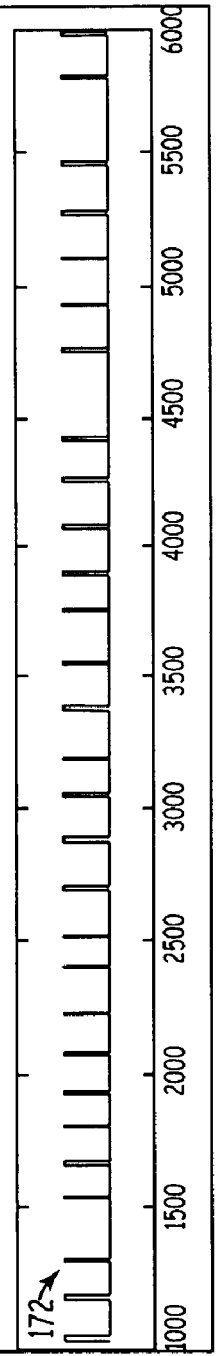
Figure 7A:
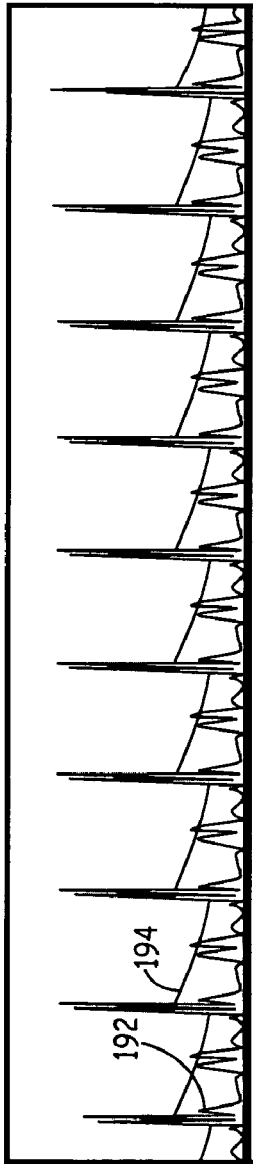
FIGS. 7A-7D are graphs illustrating sensing results of an ICD at various sensitivity settings.
Figure 7B:
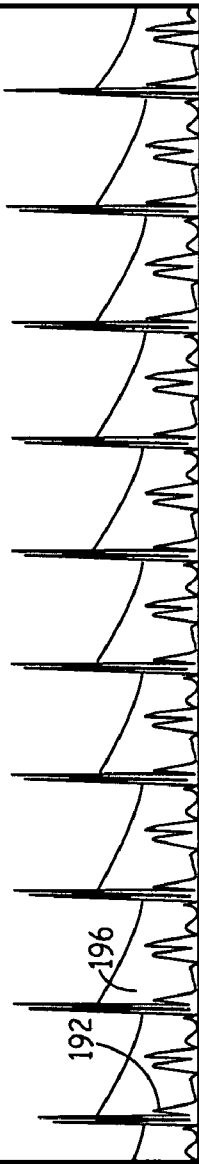
Figure 7C:
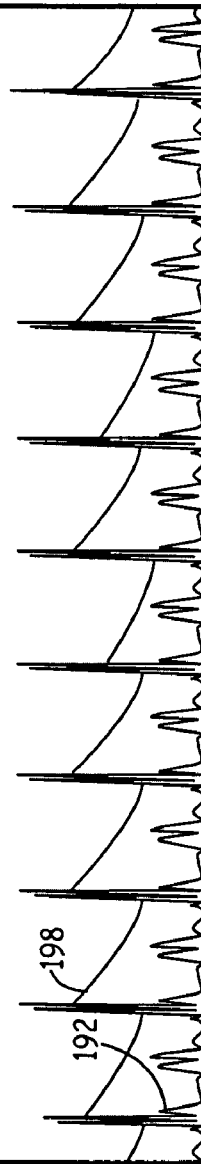
Figure 7D:
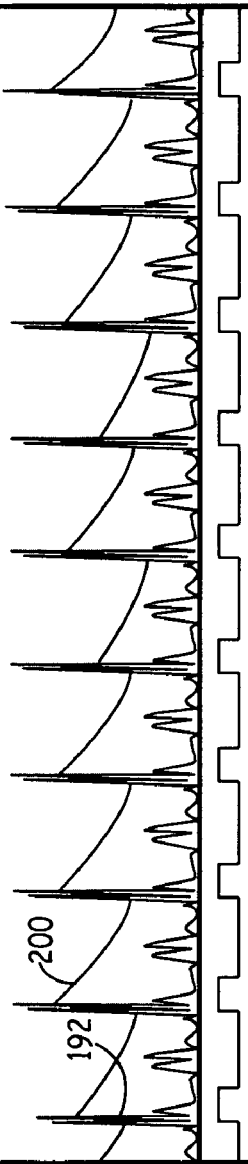

Similarly, FIGS. 6A and 6B are simulated ECG signal 160 and simulated ventricular EGM signal 162 respectively. FIG. 6C graphs filtered EGM signal 164 and 1.2 millivolts threshold signal 166. FIG. 6D is ventricular sense signal 168 corresponding to signals 164 and 166. FIG. 6E graphs filtered EGM signal 164 and 0.3 millivolts threshold signal 170. FIG. 6F is ventricular sense signal 172 corresponding to signals 164 and 170. In this example, acceptable sensing occurs at the 0.3 millivolts sensitivity setting, but undersensing occurs at the 1.2 millivolts sensitivity settings.

The present invention is not limited to the testing of ICD 12 and its sensitivity settings during implant. Rather, the method of the present invention may be used at any time following implant to provide information to a physician for use in selecting a setting for any sensing parameter of ICD 12. As the examples of FIGS. 5 and 6 illustrate, different patients will have different needs. A physically active patient may require finer oversensing adjustments than a more sedate patient due to increased heart rate caused by the exercise.

Accordingly, the sensing parameters of ICD 12 may need to be optimized for each individual patient. However, conventional methods for identifying an optimal sensitivity setting are generally tedious and often require the review of substantial amounts of data. Differently, the present invention provides the physician with better information upon which a setting for a sensing parameter may be optimized for a particular patient.

In accord with the present invention, the physician may retrieve from memory, either locally or remotely, EGM data corresponding to the occurrence of either spontaneous or induced cardiac episodes. This data may then be analyzed to simulate, or predict, how ICD 12 would have respond to the cardiac episode had it been programmed with a different setting of the sensing parameter under study. The simulation is performed by varying parameters associated with digital filters 106 (FIG. 3) and determining whether a V-sense pulse would be produced by the same EGM data if a lower sensitivity were used. By reporting the results of this simulation to the physician, the physician is better equipped to select a particular setting of the sensing parameter for the patient. This ability to analyze historical data has immense clinical significance in enabling a physician to troubleshoot past oversensing and/or undersensing and better select a setting for a particular sensing parameter that will minimize future oversensing and/or undersensing.

For instance, a safety margin may be calculated for each available setting of a particular sensing parameter, such as sensitivity. This safety margin can be calculated from the stored EGM data (or from real-time EGM data) and be based upon the likelihood of a cardiac episode be detected and/or the likelihood of oversensing occurring. The calculation of the safety margin may be implemented in firmware and/or hardware in ICD 12 itself, external programmer 90 or similar device, a remote computer connected to external programmer 90 by a communication protocol, or a combination thereof.

To improve the accuracy of this calculated safety margin, previous cardiac episodes may be evaluated, either by a physician or automatically (e.g., by ICD 12, external programmer 90 or similar device, remote computer connected to external program 90 by a communication protocol, or a combination thereof), to determine a rhythm truth for previously detected cardiac episodes (e.g., whether the cardiac episode is in fact a ventricular tachycardia or a ventricular fibrillation, or whether it is simply a supraventricular tachyarrhythmia (SVT)).

As shown in the graphs of FIGS. 7A-7D, another option for providing the physician with more information is to graphically illustrate the sensing results of ICD 12 at several different settings of a sensing parameter. The steps of graphically illustrating the sensing results may be implemented in firmware and/or hardware of external programmer 90 (or similar device) or in a remote computer connected to external programmer 90 by a communication protocol, or a combination thereof.

Presented in each of FIGS. 7A-7D is filtered ventricular EGM signal 192 and a threshold signal determined as a function of a different sensitivity setting. Threshold signal 194 of FIG. 7A corresponds to a 0.3 millivolts sensitivity setting; threshold signal 196 of FIG. 7B corresponds to a 0.45 millivolts sensitivity setting; threshold signal 198 of FIG. 7C corresponds to a 0.6 millivolts sensitivity setting; and threshold signal 200 of FIG. 7D corresponds to a 1.2 millivolts sensitivity setting. By presenting the sensing results in this format, the physician can easily and readily see the impact of different sensitivity settings on a particular patient. For instance, in the example of FIGS. 7A-7D, the patient will likely experience T-wave oversensing at the 0.3 millivolts sensitivity setting. Good improvement is seen at both the 0.45 and 0.6 millivolts sensitivity settings. In addition to the graphical representation shown in FIGS. 7A-7D, the physician may also be presented with a calculated safety margin for each setting.

Figure 8:
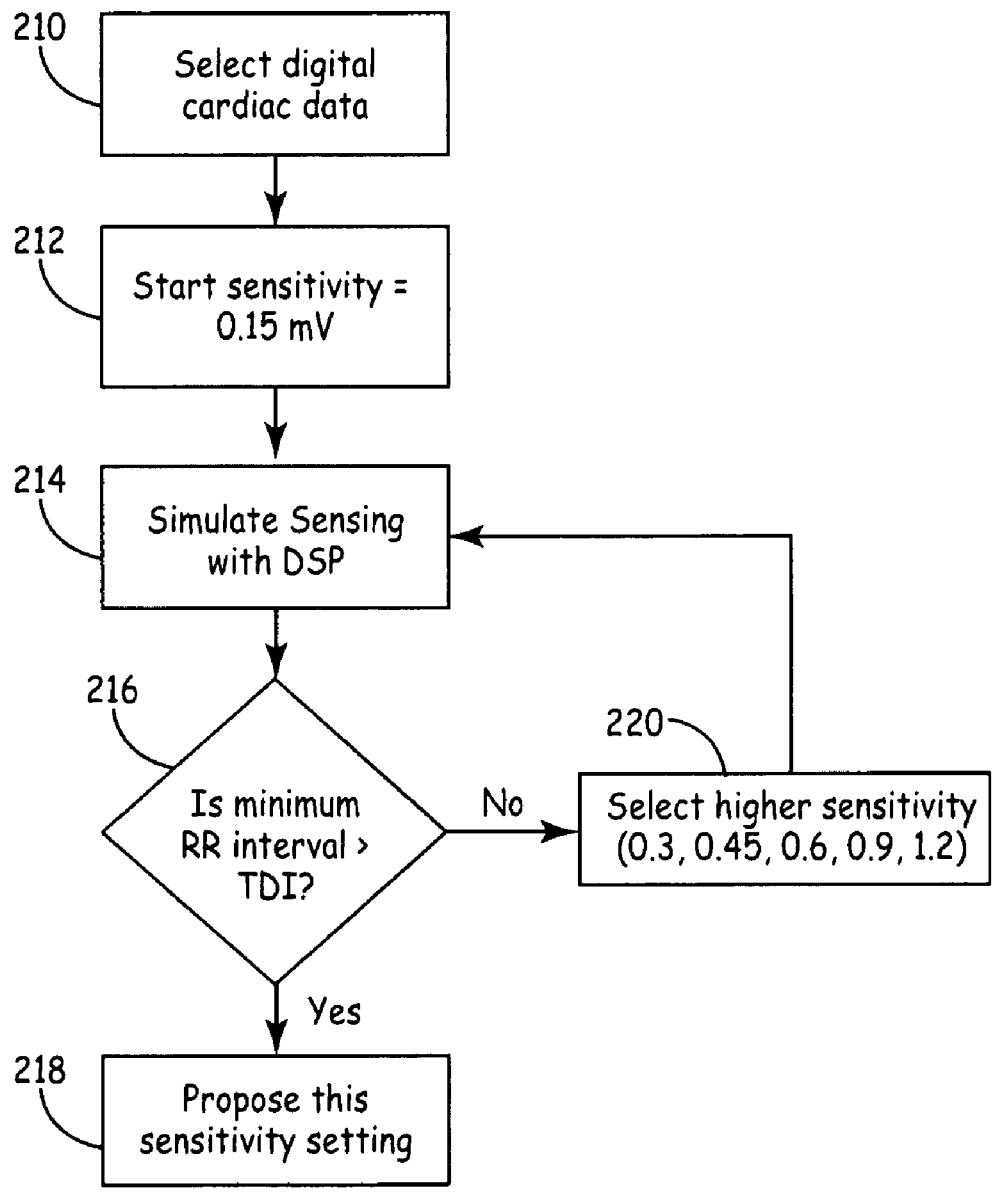
FIG. 8 is a flow chart illustrating a method in accord with the present invention for testing the sensitivity setting of an ICD.

FIG. 8 is a flow chart of a method in accord with the present invention for testing the setting of a sensing parameter (e.g., sensitivity) of ICD 12 and proposing a particular setting for the patient. The method of FIG. 8 may be implemented in firmware and/or hardware in ICD 12 itself, external programmer 90 or similar device, a remote computer connected to external programmer 90 by a communication protocol, or a combination thereof.

At step 210, the digital cardiac data upon which the analysis will be based is selected. Preferably, this data will be selected from the EGM data corresponding to at least one cardiac episode detected due to oversensing, such as a ventricular fibrillation, of the patient. For example, the data could be selected to correspond to a spontaneous cardiac event of the patient or from an induced cardiac event that occurs during the patient's initialization period during implant.

At step 212, an initial sensitivity setting to test is selected. In this example, the setting is 0.15 millivolts. At step 214, sensing by ICD 12 operating at the selected sensitivity setting is simulated by analyzing the selected digital cardiac data and sensitivity setting.

At step 216, the minimum R-R interval, defined as the time period between detected R-waves is compared to a programmable interval (TDI) or other user-defined interval. R-R intervals that fall below the TDI interval (or other user-defined interval) are suspected being the result of either fibrillation or tachycardia. Thus, if the minimum R-R interval is greater than the TDI interval (or other user-defined interval), the sensitivity should be sufficient to ensure detection of any cardiac episodes while still minimizing as best possible the likelihood of oversensing. As such, at step 218, the current selected sensitivity setting is proposed for the patient.

If, however, the minimum R-R interval is less than or equal to the TDI interval (or other user-defined interval), a new sensitivity setting to be tested is selected at step 220. Preferably, this new setting will be greater than the previous setting. In the example of FIG. 8, the available settings to be tested include 0.15, 0.3, 0.45, 0.6, 0.9, and 1.2 millivolts. Sensing is then simulated with this new sensitivity setting at step 214, with steps 214, 216, and 220 continuing until a sensitivity setting has been selected. The simulation is performed by varying parameters associated with digital filters 106 (FIG. 3) and determining whether a V-sense pulse would be produced by the EGM data if the new sensitivity were used.

Again, each of steps 210, 221, 214, 216, 218, and 220 may be implemented in firmware and/or hardware in ICD 12 itself, external programmer 90 or similar device, a remote computer connected to external programmer 90 by a communication protocol, or a combination thereof.

The present invention introduces an apparatus and method for testing the operability of an implantable cardioverter defibrillator (ICD) following its implant into a patient and for proposing personalized sensitivity settings without requiring that the ICD be reprogrammed. The present invention eliminates the need at implant to reprogram the ICD from its default 0.3 millivolts sensitivity setting to 1.2 millivolts, and then back to the default setting. This method prevents the common user error of failing to return the sensitivity setting to the default setting after testing the operability of the ICD, and consequently, minimizing the risk of a cardiac episode going undetected.

By operating the ICD at implant testing at 0.3 mV, the likelihood of underdetection of the induced cardiac event is minimized. This better ensures that the cardiac episode will promptly be detected and treated. In some circumstances, an ICD operating at a 1.2 mV sensitivity setting may not detect the cardiac episode, requiring the physicians to use manual or external shock to treat the cardiac episode, and possibly inflicting greater trauma on the patient. With the present invention, physicians can be better ensured that the induced cardiac episode will be detected and treated, while still determining how the ICD would perform at the lower sensitivity setting.

The present invention further enables various sensitivity settings to be tested on the patient—again without requiring the ICD to be reprogrammed. Past or real-time cardiac data obtained by the ICD is analyzed to either present the physician with a proposed sensitivity setting or with better information upon which the physician can make a decision.

Although the present invention has been described with reference to preferred embodiments, workers skilled in the art will recognize that changes may be made in form and detail without departing from the spirit and scope of the invention.

For example, while the above examples are shown primarily with reference to ventricular EGM signals, the present invention applies equally to any stored or real-time cardiac signals, including EGM, SubQ EGM, or ECG signals obtained from any of the right atrium, left atrium, right ventricle, or left ventricle. The present invention is not limited to determining a sensitivity setting, but equally applies to other sensing parameters in an ICD such as decay constant, percent of R-wave threshold peak, and the like. Although the present invention has been described with reference to digital embodiments, those skilled in the art will recognize that the present invention may also be used with ICDs comprising analog circuitry, digital circuitry, or a combination thereof. Although the present invention has been described with reference to an implantable cardioverter defibrillator, the present invention applies equally to other type of implantable medical devices, including pacemakers and cardiac resynchronization devices, that sense cardiac signal activity from leads attached to the heart or from subcutaneous electrodes.

The invention claimed is:

1. An apparatus for use in selecting a setting of a sensing parameter of an implantable medical device (IMD) for a patient, the apparatus comprising:
   means for obtaining, from a sensing electrode associated with the IMD, cardiac data corresponding to a cardiac episode experienced by the patient, wherein the IMD is operated at a first setting of the sensing parameter when the cardiac data is obtained;
   means for simulating, based upon the cardiac data, cardiac event identification if the IMD were operated at a second setting of the sensing parameter different than the first setting without reprogramming the sensing parameter to the second setting; and
   means for reporting the simulated cardiac event identification performance of the IMD.

2. The apparatus of claim 1 wherein the means for reporting the simulated cardiac event identification performance of the IMD comprises:
   means for generating a simulated sensing signal comprising indicators for each cardiac event identified by the means for simulating cardiac event identification;
   means for graphically displaying the cardiac data and a threshold signal determined as a function of the second setting of the sensing parameter.

3. The apparatus of claim 2 and further comprising:
   means for graphically displaying the simulated sensing signal.

4. The apparatus of claim 1 wherein the cardiac episode comprises a spontaneous cardiac episode.

5. The apparatus of claim 1 wherein the sensing parameter is a sensitivity setting of the IMD.

6. The apparatus of claim 5 wherein the first setting and the second setting are each selected from the group consisting of 0.15 millivolts, 0.3 millivolts, 0.45 millivolts, 0.6 millivolts, 0.9 millivolts, and 1.2 millivolts.

7. The apparatus of claim 1 wherein the cardiac data is representative of an EGM signal.

8. A method for testing an implantable medical device (IMD) following the implant of the IMD into a patient, the method comprising:
   inducing a cardiac episode in the patient;
   determining whether the implanted IMD, when operating at a first setting of a sensing parameter, detects the cardiac episode;
   obtaining digital cardiac data from a sensing electrode associated with the implanted IMD; and determining, from the digital cardiac data, whether the implanted IMD would detect the cardiac episode if it were operating at a second setting of the sensing parameter different than the first setting, without reprogramming the sensing parameter to the second setting.

9. The method of claim 8 and further comprising:
reporting whether the implanted IMD would detect the cardiac episode if it were operating at the second setting of the sensing parameter.

10. The method of claim 8 wherein the sensing parameter is a sensitivity setting of the IMD.

11. The method of claim 10 wherein the first setting of the sensing parameter is 0.3 millivolts.

12. The method of claim 10 wherein the second setting of the sensing parameter is 1.2 millivolts.

13. The method of claim 8 wherein obtaining digital cardiac data from a sensing electrode associated with the implanted IMD comprises:
obtaining an analog EGM signal from the sensing electrode of the implanted IMD; and
processing the analog EGM signal to determine the digital cardiac data.

14. The method of claim 8 and further comprising:
graphically displaying the digital cardiac data as a function of time.

15. The method of claim 14 and further comprising:
graphically overlaying an automatic threshold signal over the displayed digital cardiac data, wherein the automatic threshold signal is determined as a function of the second setting of the sensing parameter.

16. The method of claim 8 wherein determining, from the digital cardiac data, whether the implanted IMD would detect the cardiac episode if it were operating at a second setting of the sensing parameter different than the first setting comprises:
simulating identification of cardiac events if the IMD were operated at the second setting of the sensing parameter;
determining whether a minimum time period between identified cardiac events exceeds a user-programmed interval.

17. The method of claim 8, wherein the sensing parameter is associated with a digital filter.

18. A method for use in selecting a setting of a sensing parameter of an implantable medical device (IMD) for a patient, the method comprising:
obtaining digital cardiac data corresponding to a cardiac episode experienced by the patient;
simulating, based upon the digital cardiac data, cardiac event identification if the IMD were operated at each of a plurality of settings of the sensing parameter without reprogramming the sensing parameter to the plurality of settings; and
reporting, for each sensing parameter setting, the corresponding simulated cardiac event identification performance of the IMD.

19. The method of claim 18 wherein reporting, for each sensing parameter setting, the corresponding simulated cardiac event identification performance of the IMD comprises:
generating, for each sensing parameter setting, a simulated sensing signal comprising indicators for each cardiac event identified during the corresponding step of simulating cardiac event identification;
graphically displaying, for each sensing parameter setting, the digital cardiac data, a threshold signal determined as a function of that sensing parameter setting, and the simulated sensing signal.

20. The method of claim 18 wherein the sensing parameter is a sensitivity setting of the IMD.

21. The method of claim 20 wherein each sensing parameter setting is selected from the group consisting of 0.15 millivolts, 0.3 millivolts, 0.45 millivolts, 0.6 millivolts, 0.9 millivolts, and 1.2 millivolts.

22. A method for use in an implantable medical device (IMD), comprising:
setting a default sensitivity for sensing cardiac events;
sensing a cardiac signal;
detecting ventricular fibrillation from the sensed cardiac signal using the default sensitivity setting;
storing the cardiac signal;
performing a simulation using the stored cardiac signal to determine whether the ventricular fibrillation would have been detected if the sensitivity setting were set at a second sensitivity setting less sensitive than the default setting, without reprogramming the sensitivity setting to the second setting; and
generating a report in response to the simulation determining that the ventricular fibrillation would not have been detected if the sensitivity were set at the second sensitivity setting.

23. The method of claim 22 further comprising, computing a safety margin for each of the default setting and second setting;
wherein generating the report comprises reporting the safety margin for each of the default setting and the second sensitivity setting.

24. A method for selecting a setting of a sensing parameter of an implantable medical device for a patient, the method comprising:
selecting digital cardiac data from EGM data of the patient;
selecting a sensing parameter test setting;
analyzing the selected digital cardiac data using the selected test setting without reprogramming the IMD to the selected test setting to determine a minimum interval between R-waves of the selected cardiac data;
comparing the minimum interval to a predetermined interval corresponding to arrhythmia detection; and
reporting the test setting as a proposed sensing parameter setting to avoid oversensing in response to the minimum interval being greater than the predetermined interval.

* * * * *